United States Patent
Cooley et al.

(10) Patent No.: US 7,939,621 B2
(45) Date of Patent: May 10, 2011

(54) OLIGOCARBONATE MOLECULAR TRANSPORTERS

(75) Inventors: Christina Cooley, Palo Alto, CA (US); James Lupton Hedrick, San Jose, CA (US); Matthew Kiesewetter, Stanford, CA (US); Fredrik Nederberg, Greenville, DE (US); Brian Trantow, Mountain View, CA (US); Robert Waymouth, Palo Alto, CA (US); Paul Wender, Menlo Park, CA (US)

(73) Assignees: International Business Machines Corporation, Armonk, NY (US); Stanford University, Stanford, CA (US)

( * ) Notice: Subject to any disclaimer, the term of this patent is extended or adjusted under 35 U.S.C. 154(b) by 75 days.

(21) Appl. No.: 12/433,693

(22) Filed: Apr. 30, 2009

(65) Prior Publication Data
US 2010/0280219 A1 Nov. 4, 2010

(51) Int. Cl.
C08G 64/00 (2006.01)
C08G 63/02 (2006.01)

(52) U.S. Cl. ........ 528/196; 429/212; 429/217; 429/232; 429/330; 514/291; 528/198; 528/425; 549/228; 549/229; 560/114

(58) Field of Classification Search .................. 424/686, 424/687; 429/212, 217, 232, 330, 686, 687; 514/291; 528/196, 198, 425; 558/228, 229; 560/114

See application file for complete search history.

(56) References Cited

U.S. PATENT DOCUMENTS

| 7,312,194 | B2 | 12/2007 | Toth et al. |
| 2003/0092046 | A1 | 5/2003 | Manoharan et al. |
| 2006/0280796 | A1 | 12/2006 | Chung et al. |
| 2007/0213277 | A1 | 9/2007 | Rothbard et al. |
| 2008/0248126 | A1 | 10/2008 | Cheng et al. |

OTHER PUBLICATIONS

Haibo Xie et al. "HIghly active, hexabutylguanidinium salt/zinc bromide binary catlyst for the couplong raction of carbon dixode and epoxides" Journal of Molecular Catalysis A: Chemical vol. 250, Issues 1-2, May 2, 2006, pp. 30-34.*

Russell C. Pratt et al., "Tagging alcohols with cyclic carbonate: a versatile equivalent of (meth)acrylate for ring-opening polymerization," Chem. Commun. 2008, 114-116.
Paul A. Wender et al., "Dendrimeric Molecular Transporters: Synthesis and Evaluation of Tunable Polyguanidino Dendrimers That Facilitate Cellular Uptake," Org. Lett. 2005, vol. 7, No. 22, 4815-4818.
Russell C. Pratt et al., "Exploration, Optimization, and Application of Supramolecular Thiourea—Amine Catalysts for the Synthesis of Lactide (Co)polymers," Macromolecules, 2006, 39, 7863-7871.
Paul A. Wender et al., "An Efficient, Scalable Synthesis of the Molecular Transporter Octaarginine via a Segment Doubling Strategy," Org. Lett. 2001, vol. 3, No. 21, 3229-3232.

* cited by examiner

*Primary Examiner* — Terressa M Boykin
(74) *Attorney, Agent, or Firm* — Shumaker & Sieffert, P.A.

(57) ABSTRACT

A cyclic carbonate monomer, including:

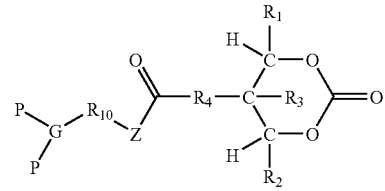

wherein
$R^1$, $R^2$, and $R^3$ are independently selected from the group consisting of H, linear or branched, substituted or unsubstituted alkyl;
$R^{10}$ is a connecting group selected from the group consisting of linear or branched, substituted or unsubstituted alkyl, heteroalkyl, cycloalkyl, heterocyclic, aryl and heteroaryl;
$R^4$ is an optional bridging group selected from the group consisting of linear or branched, substituted or unsubstituted alkyl, heteroalkyl, cycloalkyl, heterocyclic, aryl and heteroaryl;
Z is selected from the group consisting of O, NH, NR, and S;
G is a guanidine group; and
P is a protecting group.
The cylic carbonate monomer can be reacted with an initiator including a drug, drug candidate, probe or other molecule of interest to form an oligomer with the molecule of interest attached to one end of a carbonate backbone and guanidine groups attached to the carbonate backbone.

25 Claims, 12 Drawing Sheets

| Concentration (M) | Absorbance (AU) |
|---|---|
| 0.0001 | 1.5011 |
| 0.00005 | 0.73687 |
| 0.00001 | 0.15813 |
| 0.000001 | 0.016527 |

| Concentration (M) | Absorbance (AU) |
|---|---|
| 0.0001 | 1.6526 |
| 0.00005 | 0.83922 |
| 0.00001 | 0.18729 |
| 0.000001 | 0.0097547 |

OLIGOCARBONATE MOLECULAR TRANSPORTERS

This invention was made with Government support under contracts CA031841 and CA031845, awarded by the National Institutes of Health; and, under contracts 0645891 and 0213618, awarded by the National Science Foundation. The Government has certain rights in the invention.

TECHNICAL FIELD

The present disclosure relates to carbonate compositions, methods for making them, and methods for using them to transport and/or deliver therapeutics, therapeutic candidates, probes, or other molecules of interest across biological barriers.

BACKGROUND

The cellular or tissue uptake of a molecule of interest such as, for example, a drug, a diagnostic agent, a probe or the like, can be enabled or enhanced by reversibly attaching the molecule of interest to a molecular transporter compound having guanidinium functional groups. The cellular uptake of the molecule of interest can be a function of the number and/or arrangement of guanidinium groups on the molecular transporter compound. A variety of guanidinium-rich (GR) molecular transporter compounds exhibit cell-penetrating activity, and branched (dendrimeric) GR molecular transporter compounds can carry a variety of biologically useful cargos into cells and into tissues. For example, GR peptides have been used to carry drugs into human skin and cells therein. In another example, GR dendrimeric molecular transporter compounds have been used for targeted therapy and imaging applications.

However, GR peptides and GR dendrimeric molecular transporter compounds can be difficult, time consuming, and expensive to synthesize. This in turn limits their applicability in basic research, imaging, and therapy. Simplified synthetic methods for making GR molecular transporter compounds can expand the range of applications of transporters in the delivery of drugs, drug candidates, probes and molecules of interest in chemotherapy, imaging, diagnostics, and mechanistic chemical biology.

SUMMARY

The organocatalytic ring-opening oligomerization of a cyclic carbonates can be initiated by a variety of nucleophiles such as, for example, alcohols, amines or thiols, providing for the one-step synthesis of oligomers of well-defined molecular weights and narrow polydispersities.

In one aspect, the present invention is directed to an oligomerizable cyclic carbonate monomer functionalized with a guanidine group. This cyclic carbonate monomer can react with an initiator compound such as, for example, a drug, drug candidate, gene, probe or their equivalents, producing an intermediate that can react further with additional monomers or other monomers to provide a carbonate homooligomer or cooligomer. The resultant oligomer incorporates the initiator along with pendant guanidine groups attached to an oligocarbonate backbone. The protected guanidine groups on the cooligomer backbone can optionally be de-protected by reacting with an acid to provide a guanidinium rich (GR) conjugate of the molecular transporter compound and the initiator. The GR molecular transporter conjugate includes pendant guanidinium groups that can enhance transport and/or delivery of the reversibly attached cargo compound across a selected biological barrier.

A functional cyclic carbonate compound and a functionalized compound with guanidine moieties can be reacted to reproducibly synthesize the cyclic carbonate monomer product, which has a narrow range of polydispersities. When the cyclic carbonate monomer is reacted with the initiator compound, the length of the carbonate-containing backbone in the carbonate cooligomer reaction product, that is the number of monomers incorporated in the process, can be readily controlled through adjustment of the initiator-monomer ratio. The cooligomer reaction product has a narrow polydispersity, defined as the ratio of the weight average molecular weight over the number average molecular weight ($M_w/M_n$=PDI.) Preferably the PDI is less than 1.5, most preferably less than 1.2. The GR molecular transporter compound derived from the carbonate cooligomer is stable on storage and water soluble, and does not exhibit acute toxicity to cells when used for shorter time periods in biological assays or in therapeutic concentrations for extended time periods. The facile cellular uptake exhibited by the molecular transporter compounds described herein, and the ease with which short to long chain oligomers and mixed oligomers can be prepared, are advantageous for drug/probe delivery, particularly for biological cargos.

In one aspect, the present invention is directed to a cyclic carbonate monomer, including:

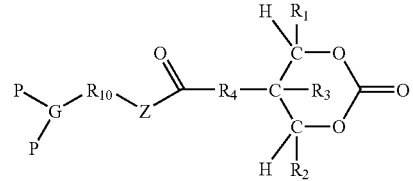

wherein $R^1$, $R^2$, and $R^3$ are independently selected from the group consisting of H, linear or branched, substituted or unsubstituted alkyl;

$R^{10}$ is a connecting group selected from the group consisting of linear or branched, substituted or unsubstituted alkyl, heteroalkyl, cycloalkyl, heterocyclic, aryl and heteroaryl;

$R^4$ is an optional bridging group selected from the group consisting of linear or branched, substituted or unsubstituted alkyl, heteroalkyl, cycloalkyl, heterocyclic, aryl and heteroaryl;

Z is selected from the group consisting of O, NH, NR, and S;

G is a guanidine group; and

P is a protecting group.

In another aspect, the present invention is directed to a method including reacting:

(i) a cyclic carbonate monomer including a cyclic carbonate backbone, and at least one guanidine group pendant from the backbone; and (ii) an initiator including a biological cargo selected from at least one of a drug, a gene and a probe; to form an oligomer including a carbonate backbone and guanidine groups attached to the carbonate backbone, wherein the biological cargo is attached to at least one end of the carbonate backbone.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
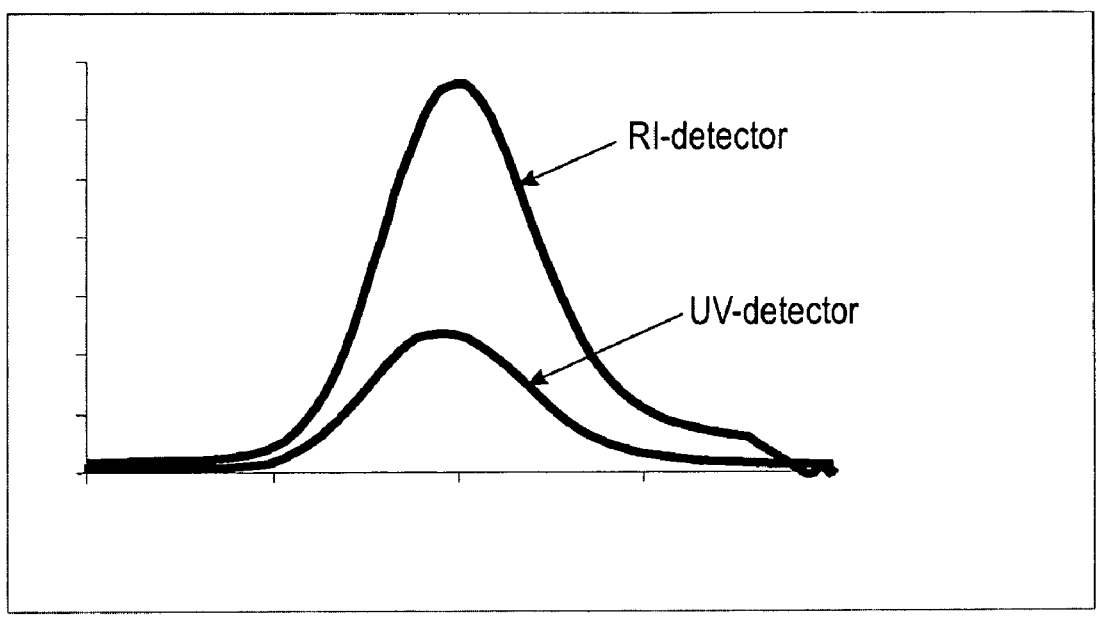
FIG. 1 is a GPC overlay of RI and UV detector spectra for Compound 5b in Reaction 2.

In one aspect, the present invention is directed to an oligomerizable cyclic carbonate monomer functionalized with a guanidine group or protected guanidinium group. This monomer is the reaction product of a functional cyclic carbonate compound and a functionalized guanidinyl compound.

The functional cyclic carbonate compound includes cyclic carbonates moieties with 5-7 carbon atoms. In this application the term carbonate refers to a compound including the carbonate ion shown in Formula 1 below, and the term cyclic carbonate compound refers to a cyclic moiety that includes the carbonate ion:

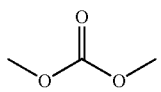

FORMULA 1

In a preferred embodiment shown in Formula 2 below, the functional cyclic compound includes a cyclic carbonate moiety with a 6-membered ring:

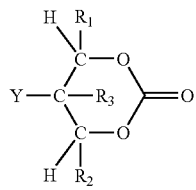

FORMULA 2

In Formula 2, $R^1$, $R^2$ and $R^3$ may be independently selected from H, linear or branched, substituted or unsubstituted alkyl, or aryl. $R^1$ and $R^2$ are preferably H, and $R^3$ is preferably CH$_3$. Referring again to Formula 2, Y is a functional group that can vary widely depending on the functionality of the guanidinyl compound with which the cyclic carbonate compound is to be reacted. Suitable functional groups include acyl groups such as carboxylic acids, acid chlorides, anhydrides, amides, esters, and the like. For example, a preferred functional group Y for the cyclic carbonate compound of Formula 2 is carboxylic acid derivative shown below in Formula 3:

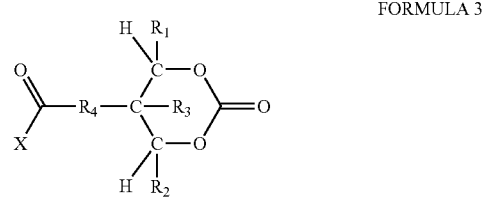

FORMULA 3

In Formula 3, $R^4$ is an optional bridging group that may be linear or branched, substituted or unsubstituted alkyl, heteroalkyl, cycloalkyl, heterocyclic, aryl and heteroaryl, and preferably $R^4$ is linear alkyl or cycloalkyl. In Formula 3, X may be, for example, OH, OC(O)R, Cl, Br, I, OR, or some other functional group that renders the carboxylic acid derivative an activated ester.

The functionalized guanidinyl compound includes at least one guanidine group and at least one functional group. In this application the term guanidine or guanidinyl group refers to a moiety having the structure shown in Formula 4 below, and the term guanidinium group refers to a positively charged conjugate acid form thereof:

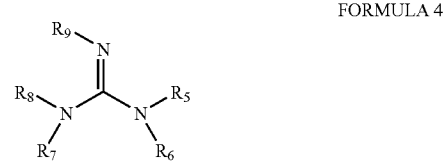

FORMULA 4

In Formula 4, $R^6$ and $R^7$ are preferably H, while $R^5$ and $R^8$ are preferably protective groups selected from, for example, Boc urethane (Boc=C(O)OtBu), or benzyl (CH$_2$Ph).

In Formula 4, $R^9$ can vary widely depending on the intended application, and in the functionalized guanidinyl compound $R^9$ is a functional group selected to react with the functional group Y on the cyclic carbonate compound of Formula 2 above. For example, if an acid chloride is selected as the functional group Y on the cyclic carbonate compound (Formula 2), suitable functional groups $R^9$ for the guanidinyl compound include at least one hydroxy, thio or amino group, preferably a linear or branched, substituted or unsubstituted aliphatic hydroxy, thio or amino group. An exemplary guanidinyl compound is shown in Formula 5 below:

FORMULA 5

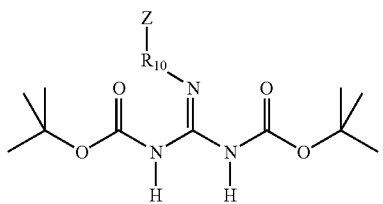

In Formula 5, $R^{10}$ is linear, substituted or unsubstituted alkyl, and Z is OH, $NH_2$, or SH.

The functional cyclic carbonate compound and the functional guanidinyl compound may be reacted to produce an oligomerizable cyclic carbonate monomer, which is functionalized with a guanidine group. The cyclic carbonate monomer includes a cyclic carbonate and at least one guanidine group pendant from the cyclic carbonate. For example, if the compound of Formula 3 above is reacted with the compound of Formula 5 above, the resulting cyclic carbonate monomer is shown in Formula 6:

FORMULA 6

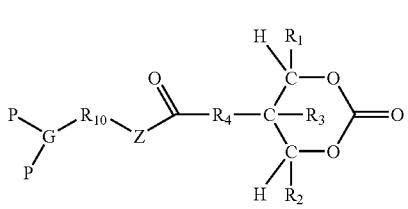

In Formula 6, $R^1$, $R^2$, $R^3$ and $R^{10}$ are independently selected from H, linear or branched, substituted or unsubstituted alkyl, with $R^1$ and $R^2$ preferably H, $R^3$ preferably $CH_3$, and $R^{10}$ preferably alkyl. The optional bridging group $R^4$ may be linear or branched, substituted or unsubstituted alkyl, heteroalkyl, cycloalkyl, heterocyclic, aryl and heteroaryl, and $R^4$ is preferably alkyl. G is a guanidine group, and P is a protecting group selected from a Boc urethane or a benzyl group, and Z is O, NH, or S, with Z preferably O.

The guanidinyl functional oligomerizable cyclic carbonate monomer may be oligomerized in the presence of a suitable catalyst and an initiator compound. In this reaction, the cyclic ring on the cyclic carbonate monomer backbone is opened and the first and second monomers are linked to provide a homooligomer or cooligomer with a carbonate backbone, pendant guanidine groups attached to the backbone, and the initiator at one end of the oligomer.

The initiator compound should be a nucleophile and can include any amino, hydroxy or thiol functional group to initiate the ring opening oligomerization step. Suitable examples include amines, alcohols, thiols, and amino alcohols including, but not limited to, aliphatic linear amino alcohols, as well as multifunctional branched systems (e.g., diethanol amine), hyperbranched and dendritic systems containing amino, hydroxy or thiol functional groups, aminophenols, amine functional peptides and related biomolecules, substituted alkoxyamines, functionalized semicarbazides, functionalized hydrazines, aminoalkoxysilanes, amino or hydroxy terminated oligomers such as, for example, (meth) acrylates, styrenes, polyethers such as, for example, PEGs, THF, and PPO-Jeffamine, and polybutadienes and the like that can be easily synthesized.

The initiator compound can optionally include a biological cargo such as, for example, a drug, a gene, a probe, or other biologically useful compound, which may be attached to one or both ends of the backbone.

Suitable catalysts include any of a family of organic catalysts including N-heterocyclic carbenes, 1,5,7-triazabicyclo [4.4.0]dec-5-ene (TBD), thiourea/amines, phosphazenes, or any of a family of metal alkoxides known in the art, such as LiOR, tin octoate, $Al(OR)_3$, LZnOR, and the like, with R selected from a linear or branched substituted or unsubstituted alkyl or acyl, and L selected from an alkoxide OR, a β-diketiminate [ArNCHRCHCHRNAr] with Ar selected from a substituted or unsubstituted aryl, or a tridentate diamino aryloxide such as 2,4,-di-tertbutyl, 6-[2-(dimethylaminoethyl)methylamino] methyl phenolate.

Preferably, the catalysts for the oligomerization are combinations of thioureas ArNHC(S)NHR', and tertiary amines or diamines, where Ar can be any substituted or unsubstituted aryl and R' can be any substituted or unsubstituted aryl or alkyl. Most preferably, the thiourea is derived from an aryl compound such as 3,5-trifluoromethylphenyl, 3,5-dinitrophenyl, napthyl and R' is a secondary alkyl such as cyclohexyl, cyclopentyl, or the like.

To form the homooligomer or a cooligomer, the guanidinyl functional cyclic carbonate monomer may also optionally be reacted with at least one second monomer. The second monomer can include a wide variety of functional groups such as, for example, protected thiol, amine, hydroxyl or acid functional groups. Alternatively, the second monomer can include a drug, a gene, a probe, or other biologically useful compound. The guanidinyl functional cyclic carbonate monomer, or the cooligomer formed by reacting the guanidinyl cyclic carbonate monomer with the second monomer, may optionally be further reacted with a third monomer with functional groups selected to modify and/or enhance the properties of the homooligomer or cooligomer, and it is not necessary that the third monomer include a biological cargo.

In a preferred embodiment, the second or third monomer is a 5- 7-membered functionalized or unfunctionalized cyclic carbonate. An exemplary monomer has the structure shown in Formula 7:

FORMULA 7

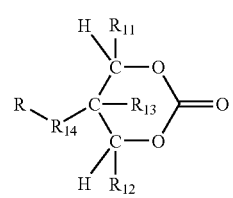

In Formula 7, $R^{11}$, $R^{12}$ and $R^{13}$ may be independently selected from H, linear or branched, substituted or unsubstituted alkyl, or aryl, and $R^1$ and $R^2$ are preferably H, and $R^{13}$ is preferably $CH_3$. The optional bridging group $R^{14}$ may be linear or branched, substituted or unsubstituted alkyl, heteroalkyl, cycloalkyl, heterocyclic, aryl and heteroaryl, and $R^4$ is preferably alkyl. F is a functional group that can vary widely to enable the coupling with peptides, proteins or other biological agents or to control the solubility of the GR oligocarbonate transporter. Suitable functional groups include acyl groups such as carboxylic acids, amides, esters, and the like, and protected thiol, amine, or hydroxyl groups. Alternatively, F can include a drug, a gene, a probe, or other biologically useful compound.

The oligomerization reaction described above preferably provides a degree of oligomerization (DP) ranging from 4 to 350, with a particularly preferred DP ranging from 6 to 25.

In a preferred embodiment, the guanidine functional cyclic carbonate monomer is reacted with an initiator compound. The initiator compound includes an amino, hydroxy or thiol functional group, and optionally further includes a biological cargo such as, for example, a drug, a gene, a probe, or other biologically useful compound or their equivalents.

For example, as shown in Reaction 1 below, if the monomer of Formula 6 is reacted with an initiator including a biologically useful compound (B), the resulting carbonate cooligomer reaction product includes multiple protected guanidinyl groups pendant from a carbonate-containing backbone scaffold, as well as a biologically useful cargo compound on at least one end of the backbone.

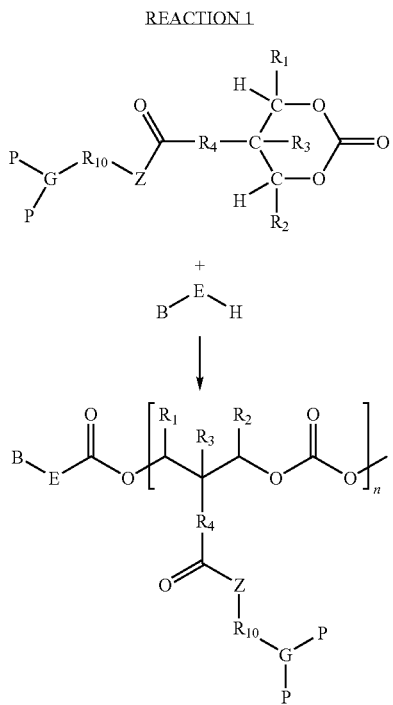

In Reaction 1, $R^1$, $R^2$, $R^3$ and $R^{10}$ are independently selected from H, linear or branched, substituted or unsubstituted alkyl, with $R^1$ and $R^2$ preferably H and $R^3$ preferably $CH_3$, $R^4$ is an optional bridging group that may be alkyl, substituted or unsubstituted alkyl, or aryl, preferably alkyl, G is a guanidinyl group, P is a protecting group selected from, for example, Boc urethane (Boc=C(O)OtBu), or benzyl ($CH_2Ph$), E is O, S or NH, preferably O, and B is a biologically useful group.

Depending on the reactants selected and the reaction conditions employed, the carbonate cooligomer may include a few monomeric units (also referred to herein as oligomers such as dimers, trimers and tetramers), a plurality of monomeric units (also referred to herein generally as oligomers), and/or compounds that themselves have multiple branches.

For example, n in the carbonate cooligomer of Reaction 1 may vary widely from about 4 to about 350, and typically n ranges from about 1 to about 50, more preferably about 5 to about 25, and most preferably from about 8 to about 22.

As a more detailed example, in an embodiment discussed in detail in the examples below, a guanidinyl functional oligomerizable cyclic carbonate monomer of Formula 8, MTC-ethylguanidine-BOC, may be reacted with the amino functional initiator compound of Formula 9,5-(dimethylamino)-N-(2-hydroxyethyl)naphthalene-1-sulfonamide, to produce the oligocarbonate compound of Formula 10, PMTC-guanidine-boc:

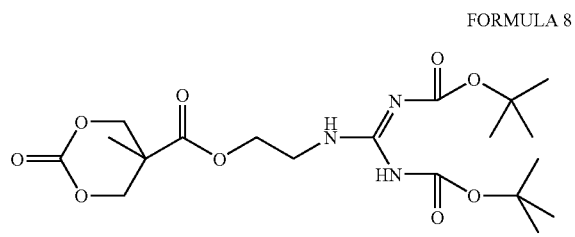

FORMULA 8

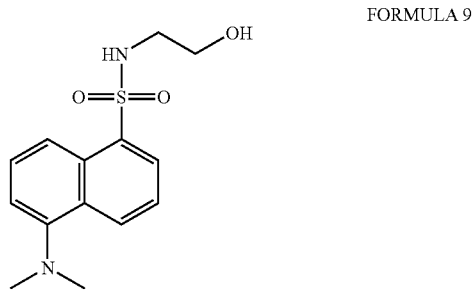

FORMULA 9

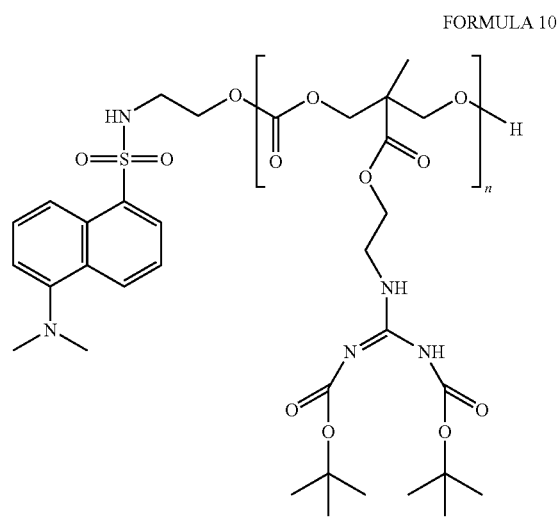

FORMULA 10

The carbonate cooligomer may optionally be reacted with an acid to remove the protecting groups P on the guanidine groups (Formula 6 and Reaction 1), which produces a guanidinium rich (GR) molecular transporter conjugate compound as a reaction product. For example, as shown in Formula 11 below, after reacting with the acid trifluoroacetic acid (TFA), the GR molecular transporter conjugate compound derived from the carbonate oligomer of Formula 10 includes pendant guanidinium groups that can enhance transport and/or delivery of the reversibly attached cargo compound across a selected biological barrier.

FORMULA 11

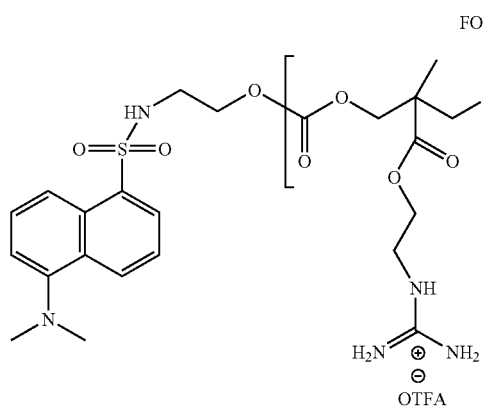

The molecular transporter conjugate compounds shown in Formula 11 above incorporate a backbone scaffold (carbonate) and side chain spacing (1,7) previously unexplored in cell uptake studies. These compounds are stable in Hepes buffered saline (pH 7.4) for hours at 37° C. as needed for their administration, and do not exhibit acute toxicity in the Jurkat cell line under the conditions of the biological assays ($\leq 25$ μM, 5 min incubation, viability greater than 80%) or when used at therapeutic concentrations for longer exposure times. Like their oligoarginine counterparts, these transporters are highly water-soluble, but they readily partition into octanol (a membrane polarity surrogate) when treated with sodium laurate, a model membrane constituent.

Reaction 2 illustrates a preferred embodiment of a one-step oligomerization strategy according to one aspect of the present invention. This strategy enables the direct introduction of probes and, by analogy, drug moieties in the same synthetic operation.

REACTION 2

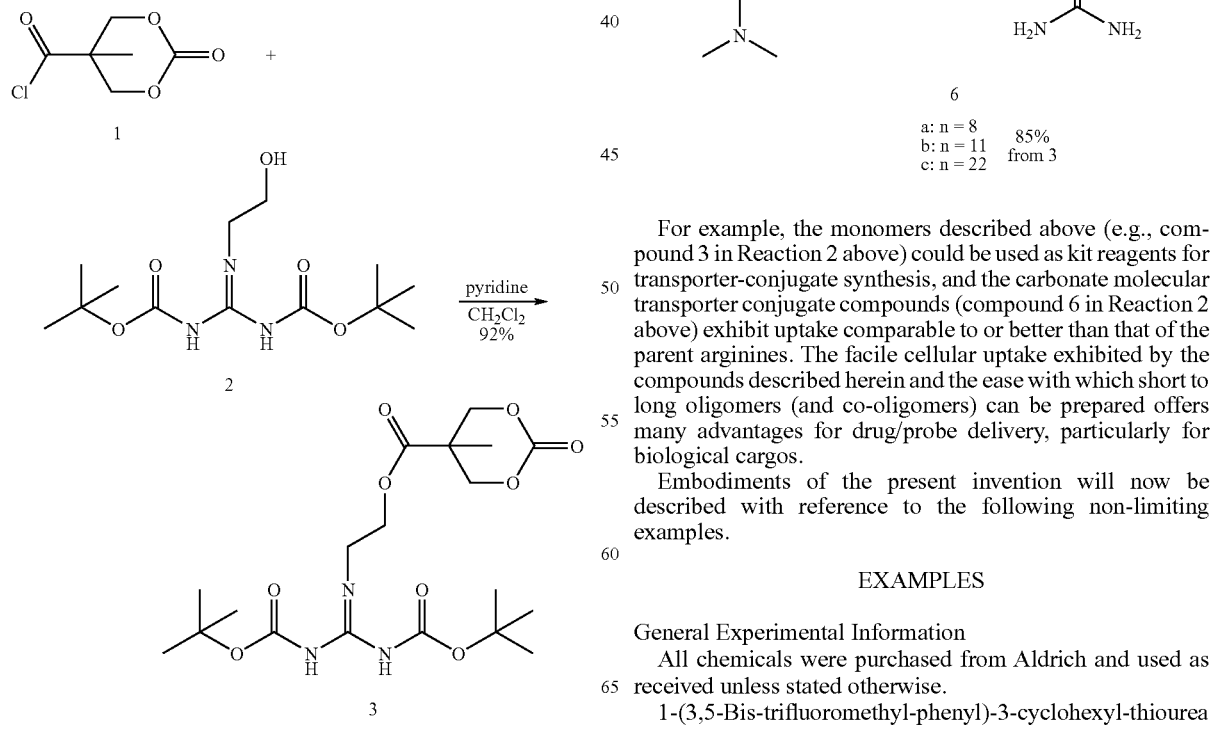

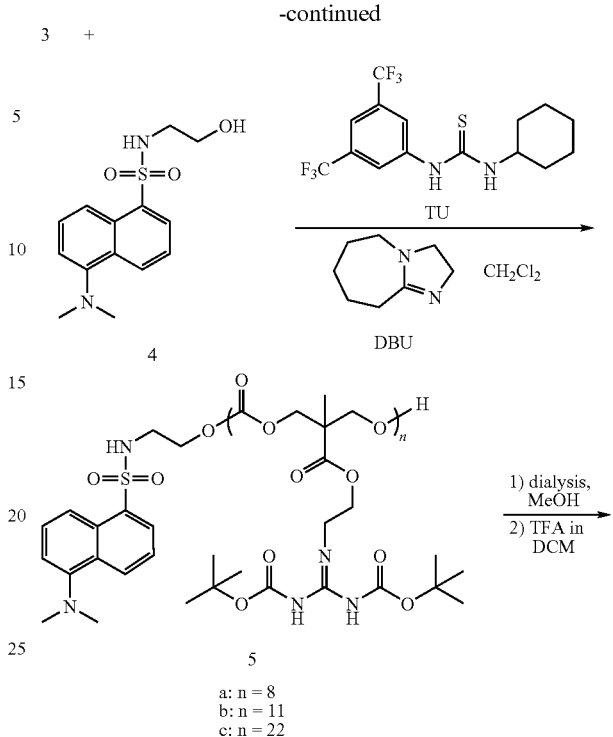

For example, the monomers described above (e.g., compound 3 in Reaction 2 above) could be used as kit reagents for transporter-conjugate synthesis, and the carbonate molecular transporter conjugate compounds (compound 6 in Reaction 2 above) exhibit uptake comparable to or better than that of the parent arginines. The facile cellular uptake exhibited by the compounds described herein and the ease with which short to long oligomers (and co-oligomers) can be prepared offers many advantages for drug/probe delivery, particularly for biological cargos.

Embodiments of the present invention will now be described with reference to the following non-limiting examples.

EXAMPLES

General Experimental Information

All chemicals were purchased from Aldrich and used as received unless stated otherwise.

1-(3,5-Bis-trifluoromethyl-phenyl)-3-cyclohexyl-thiourea (TU) was prepared according to the procedures outlined in Pratt, et al., *Macromolecules*, 2006, 39, 7863-7871, and octoarginine (r8) was prepared according to literature procedures outlined in Wender, et al., *Org. Lett.*, 2001, 3, 3229-3232.

Dansyl aminocaproic acid NHS ester was obtained from Invitrogen, Carlsbad, Calif.

Methylene chloride was stirred over $CaH_2$ overnight, degassed by three freeze-pump-thaw cycles and vacuum transferred into a flame-dried bomb.

Gel permeation chromatography (GPC) was performed in tetrahydrofuran (THF) at a flow rate of 1.0 mL/min on a Waters chromatograph equipped with four 5 μm Waters columns (300 mm×7.7 mm) connected in series.

A Viscotek (Houston, Tex.) S3580 refractive index detector and Viscotek GPCmax autosampler were employed. The system was calibrated using monodisperse polystyrene standards (Polymer Laboratories and Varian, Inc., Palo Alto, Calif.).

NMR spectra were recorded on Varian INOVA 500 MHz and Varian Mercury 400 MHz magnetic resonance spectrometers.

Synthetic Procedures 1. 5-(dimethylamino)-N-(2-hydroxyethyl)naphthalene-1-sulfonamide (Compound 4 in Reaction 2)

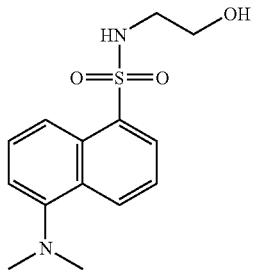

Under nitrogen, dansyl chloride (5.05 g, 18.72 mmol) was placed in a dry 250 mL round bottom flask equipped with a stir bar. Dry methylene chloride (50 mL) was added via syringe, the flask attached to an addition funnel and the system cooled to 0° C. Ethanolamine (1.25 g, 1.24 mL, 20.59 mmol), triethylamine (2.27 g, 3.13 mL, 22.46 mmol), and 75 mL of dry methylene chloride were loaded into the addition funnel, and the solution was added dropwise with stirring over 30 min. The solution was stirred for an additional 30 min before the ice bath was removed, the solution allowed to reach ambient temperature and left to stir for an additional 14 hours.

The product was isolated using flash chromatography initially eluting with methylene chloride before gradually increasing the polarity to 5% methanol in methylene chloride. Following removal of the solvent, a yellow oil was obtained that solidified upon standing. Yield 5.0 g (83%). $^1$H-NMR ($CDCl_3$) δ: 8.6-7.2 (m, 6H, ArH—), 5.45 (t, 1H, —NH), 3.62 (m, 2H, —$CH_2OH$), 3.07 (m, 2H, —$NHCH_2$—), 2.90 (s, 6H, (—$CH_3$)$_2$), 2.25 (bs, 1H, —OH).

2. MTC-ethylguanidine-BOC (Compound 3 in Reaction 2)

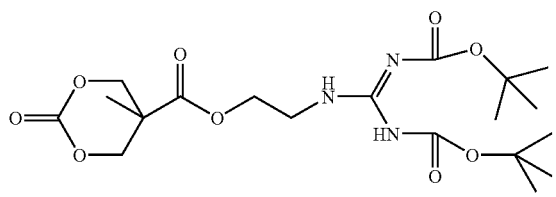

5-Methyl-2-oxo-[1,3]dioxane-5-carboxylic acid (MTC—OOH) (1.26 g, 7.9 mmol) was initially converted to MTC-Cl using standard procedures with oxalylchloride as outlined in Pratt, et al., *Chem. Commun.*, 2008, 114-116. In a dry 250 mL round bottom flask equipped with a stir bar, the formed intermediate was dissolved in 75 mL of dry methylene chloride. Under nitrogen flow, an addition funnel was attached into which 1,3-di-boc-2-(2-hydroxyethyl)guanidine (2.0 g, 5.59 mmol), pyridine (0.55 g, 0.56 mL, 6.92 mmol), and 30 mL of dry methylene chloride was charged. The flask was cooled to 0° C., and the solution was added dropwise over 30 min. The formed solution was stirred for an additional 30 min before the ice bath was removed, and the solution stirred for an additional 4 hours under nitrogen. The crude product was placed directly onto a silica gel column, and the product separated by eluting with 100% ethyl acetate. The product fractions were removed and the solvent evaporated to yield the product as white crystals. Yield 2.70 g (92%). $^1$H-NMR ($CDCl_3$) δ: 11.5 (s, 1H, NH), 8.65 (t, 1H, NH), 4.70 (d, 2H, $CH_2$), 4.35 (t, 2H, $CH_2$), 4.23 (d, 2H, $CH_2$), 3.75 (q, 2H, $CH_2$), 1.55 (s, 18H, $CH_3$), 1.45 (s, 3H, $CH_3$). HR-MS-ESI: m/z calculated for $C_{19}H_{31}N_3O_9$+Na 468.45 found 468.1952.

3. Synthesis of (PMTC-guanidine-boc) (Compound 5 in Reaction 2):

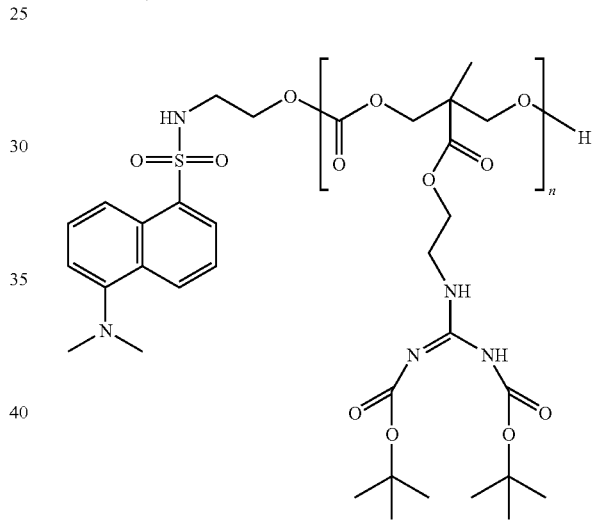

Representative Example 5b

In a glove box with $N_2$ atmosphere using flame dried glassware TU (21 mg, 56 μmol), 1,8-Diazabicyclo[5.4.0]undec-7-ene (DBU) (8.5 mg, 56 μmol), and Compound 4 (33 mg, 112 μmol) were charged in a 20 mL glass vial equipped with a stir bar. A small volume of methylene chloride was added, and the formed solution stirred for 10 minutes. MTC-guanidine-boc (0.5 g, 1.12 mmol) (Compound 3) dissolved in enough additional DCM for a final concentration of 1M monomer was added to the catalyst/initiator solution, and the resulting solution kept stirring for three hours (conversion studied by $^1$H NMR analysis). Benzoic acid (15 mg, 120 μmol) was added to quench the catalyst. The crude reaction solution was transferred into a dialysis bag (1,000 g/mol cut off), dialyzed against methanol for 48 hours, and the methanol solution was changed after 24 hours. The remaining solvent was evaporated yielding Compound 5b in Reaction 2 (0.425 g, 5b) as an off white solid.

Figure 2:
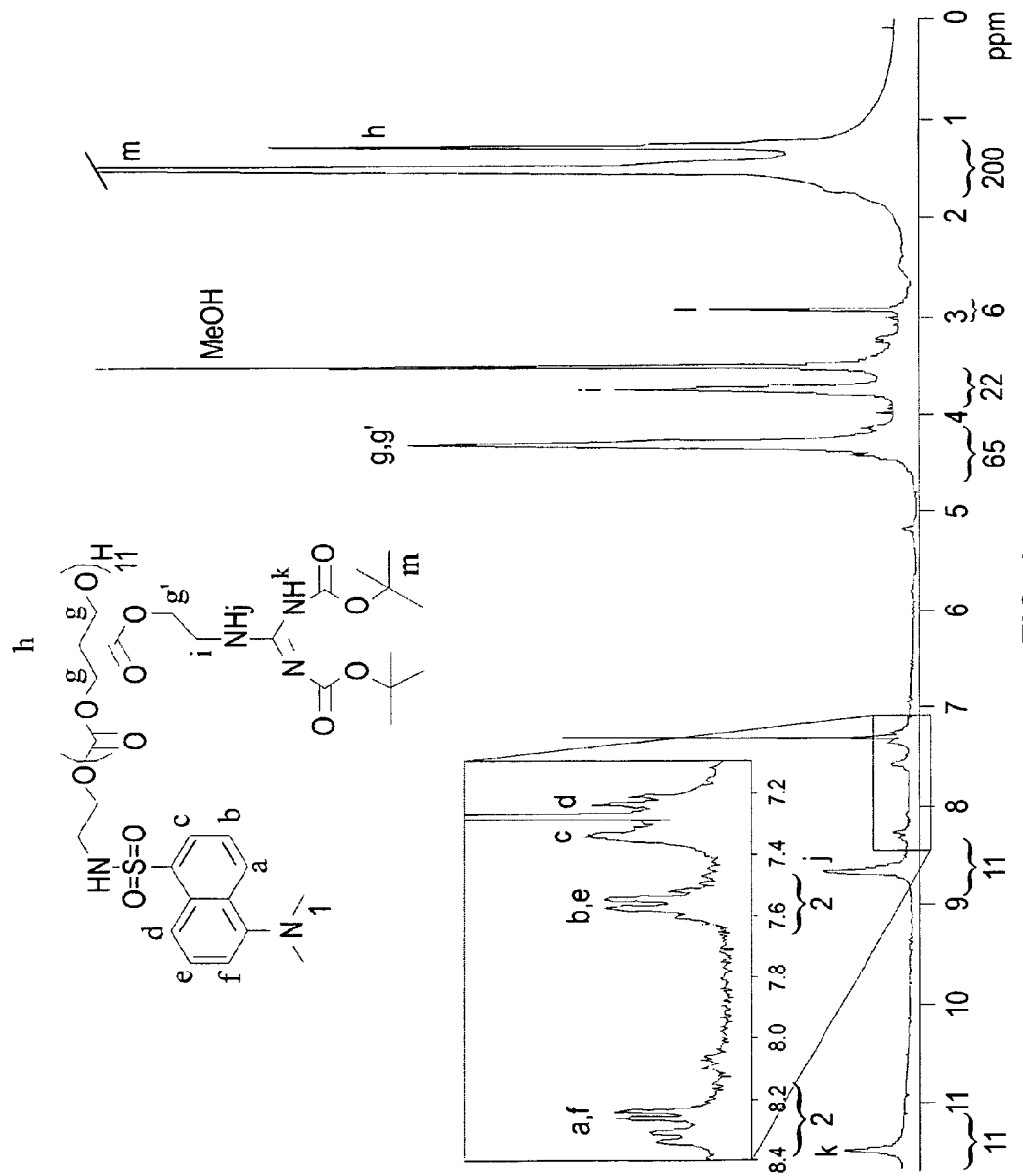
FIG. 2 is a $^1$H NMR spectrum of Compound 5b in Reaction 2.

The $^1$H-NMR spectra ($CDCl_3$) of Compound 5b are shown in FIG. 2, with integrations displayed below selected resonances. Degree of oligomerization was determined by integration of the end group resonances (i.e., b and e) v. the oligomer backbone g and g'. δ: 11.49 (s, 11H, NH), 8.66 (t, 11H, NH), 8.32 (d, 1H, ArH), 8.26 (d, 1H, ArH), 7.58 (m, 2H, ArH), 7.34 (m, 1H, ArH), 7.23 (d, 1H, ArH), 4.30 (m, 65H, polyMTC-CH$_2$), 4.14 (t, 2H, CH$_2$), 3.75 (m, 22H, polyMTC-CH$_2$), 3.22 (q, 2H, CH$_2$), 2.92 (s, 6H, CH$_3$), 1.51 (s, 200H, CH$_3$-boc), 1.28 (s, 3H, polyMTC-CH$_3$).

The syntheses of Compounds 5a and 5c (Reaction 2) were carried out analogously. For 5a, amount of Compound 4=41.5 mg, (141 µmol). For 5c, amount of dansyl ethanol=15.0 mg, (51 µmol)

TABLE 1

Characterization of PMTC-guanidine-boc oligomers:

|    | n  | $M_n$(NMR) | $M_n$(GPC) | PDI[a] |
|----|----|-----------|-----------|------|
| 5a | 8  | 3,854     | 3,029     | 1.16 |
| 5b | 11 | 5,189     | 3,160     | 1.11 |
| 5c | 22 | 10,084    | 4,692     | 1.15 |

PDI = $M_w/M_n$

FIG. 1 shows a GPC overlay of RI and UV detector spectra of Compound 5b.

PMTC-guanidine-boc (Compound 5b in Reaction 2) (0.23 g, 46 µmol) was charged in a 100 mL round bottom flask equipped with a stir bar and dissolved in 18 mL of methylene chloride. Trifluoroacetic acid (TFA) (2 mL) was added and the flask sealed and left under stirring at ambient temperature for 18 hours. Nitrogen gas was bubbled through the solution for 30 minutes and the remaining solvent evaporated by rotational evaporation yielding (0.20 g, 85%) of Compound 6b as a slightly yellow waxy solid. $^1$H-NMR (DMSO-d$_6$) δ: 8.40 (d, 1H, ArH), 8.20 (m, 2H, ArH), 7.90 (bs, 11H, polyMTC-NH), 7.55 (m, 2H, ArH), 7.25 (bs, 44H, polyMTC-NH), 7.18 (m, 44H, polyMTC-CH$_2$), 4.02 (m, 22H, polyMTC-CH$_2$), 3.92 (t, 2H, CH$_2$), 3.37 (m, 22H, polyMTC-CH$_2$), 2.99 (q, 2H, CH$_2$), 2.79 (s, 6H, CH$_3$), 1.10 (s, 33H, polyMTC-CH$_3$).

Figure 3:
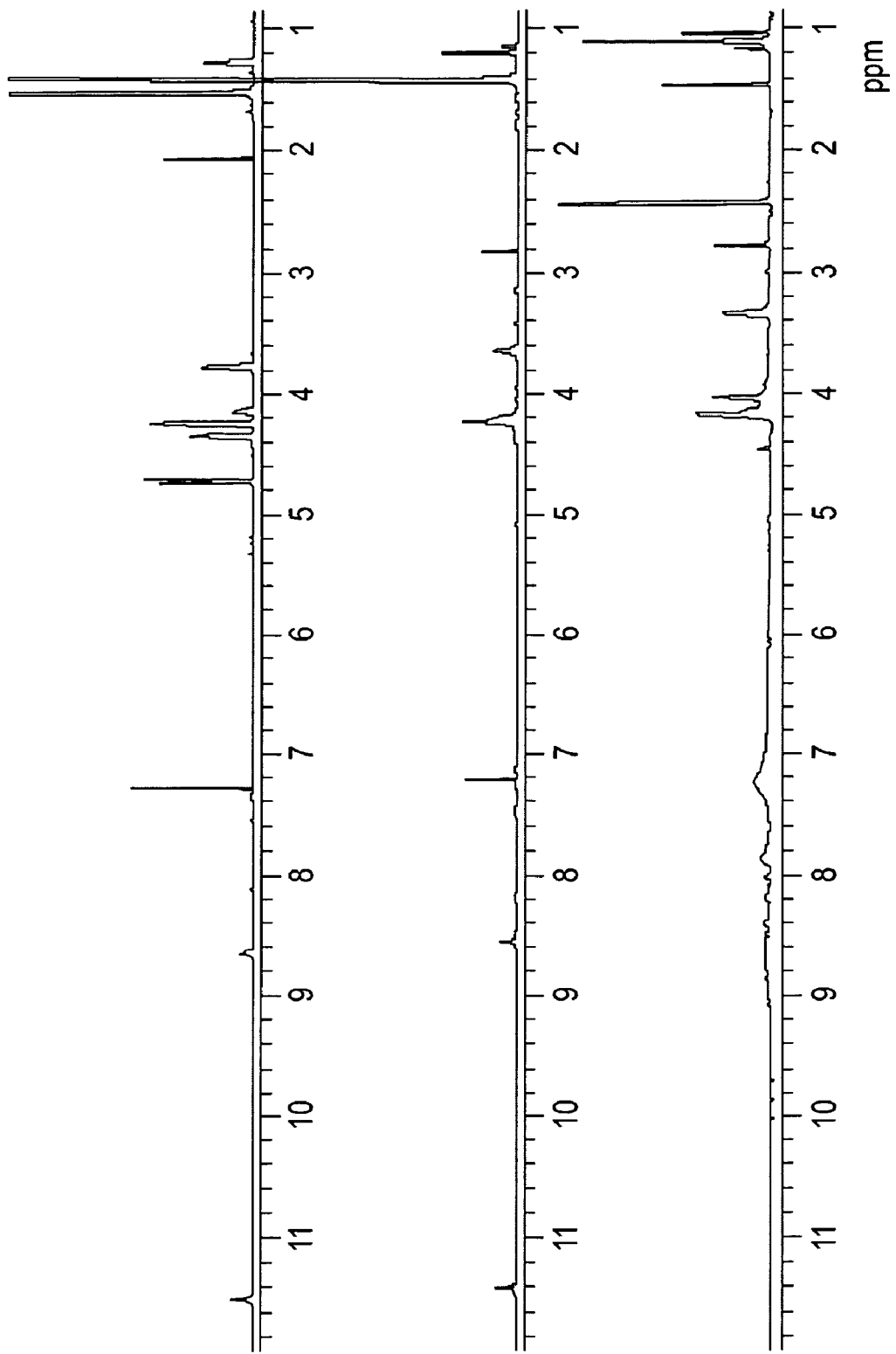
FIG. 3 shows the stacked 1H-NMR spectra of MTC-ethylguanidine-boc (Compound 3 in Reaction 2) (top, CDCl$_3$), PMTC-guanidine-boc (Compound 5 in Reaction 2) (mid, CDCl$_3$), and PMTC-guanidine (Compound 6 in Reaction 2) (below, DMSO-d6).

FIG. 3 shows stacked 1H-NMR spectra of MTC-ethylguanidine-boc (Compound 3) (top, CDCl$_3$), PMTC-guanidine-boc (Compound 5) (mid, CDCl$_3$), and PMTC-guanidine (Compound 6) (below, DMSO-d6).

5. Synthesis of Dansyl-r8

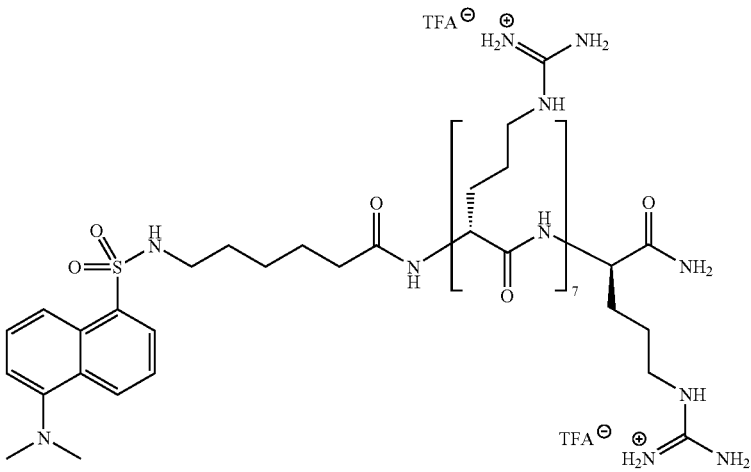

4. Synthesis of PMTC-guanidines (Compound 6 in Reaction 2)

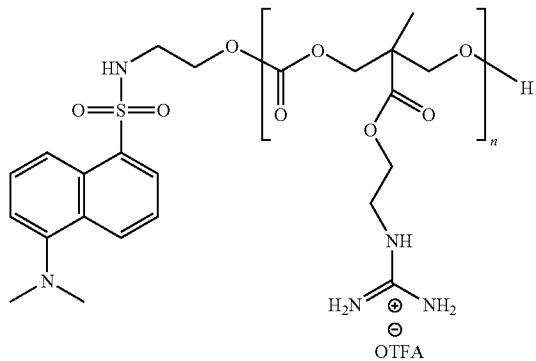

Octoarginine (25 mg, 0.01834 mmol) was added to a small conical vial with stirbar and deionized water, then lyophilized. Dansyl aminocaproic acid NHS ester (10 mg, 0.021668 mmol, Invitrogen) was dissolved in 100 µL DMF and added to the conical vial. Diisopropylethylamine (2.8 µL, 0.16251 mmol) was added and the reaction stirred at room temperature for 22.4 hours, when DMF was blown off with a stream of nitrogen. Acetonitrile (0.5 mL) and dionized water (1.5 mL) were added, followed by trifluoroacetic acid (1.7 µL, 20 equivalents), and the reaction was purified by reverse-phase HPLC (H$_2$O:CH$_3$CN, 5-60% gradient).

The product containing fractions were collected and lyophilized to yield dansyl r8 (25 mg, 90%) as a white/yellow amorphous solid; Prep RP-HPLC (H$_2$O:CH$_3$CN)>95% purity. $^1$H NMR (400 MHz, D$_2$O): δ=8.652 (d, J=8.70 Hz, 2 H), 8,424 (d, J=8.74, 1 H). 8.306 (d, J=6.98, 2 H), 7.93 (d, J=7.71, 1 H), 7.85-7.80 (m, 3 H), 4.33-4.18 (m, 8 H), 3.354 (s, 6 H), 3.18-3.11 (m, 14 H), 2.896 (t, J=6.61, 2 H), 2.116 (t, J=7.17, 3 H), 1.84-1.58 (m, 29 H), 1.38-1.29 (m, 4 H), 1.137 (d, J=7.39, 3 H) ppm.

MALDI MS: [M]+ calculated for $C_{66}H_{129}N_{35}O_{11}S$ (no TFA), 1620.04; found, 1615.365.

Figure 4:
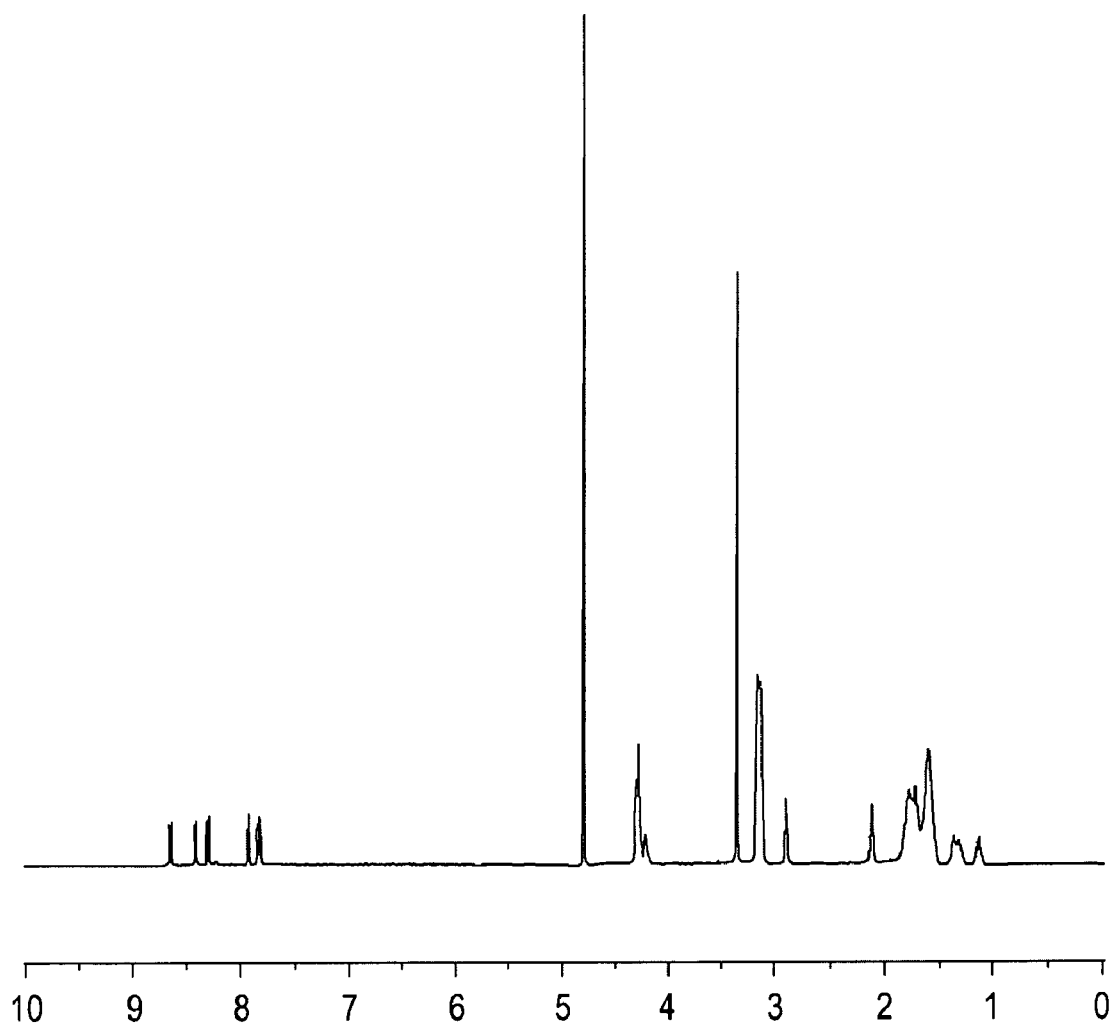
FIG. 4 is the $^1$H NMR spectrum of r8 dansyl, D$_2$O.

FIG. 4 shows the $^1H$ NMR spectrum of r8 dansyl, $D_2O$.

6. Octanol-Water Partitioning

Figure 5A:
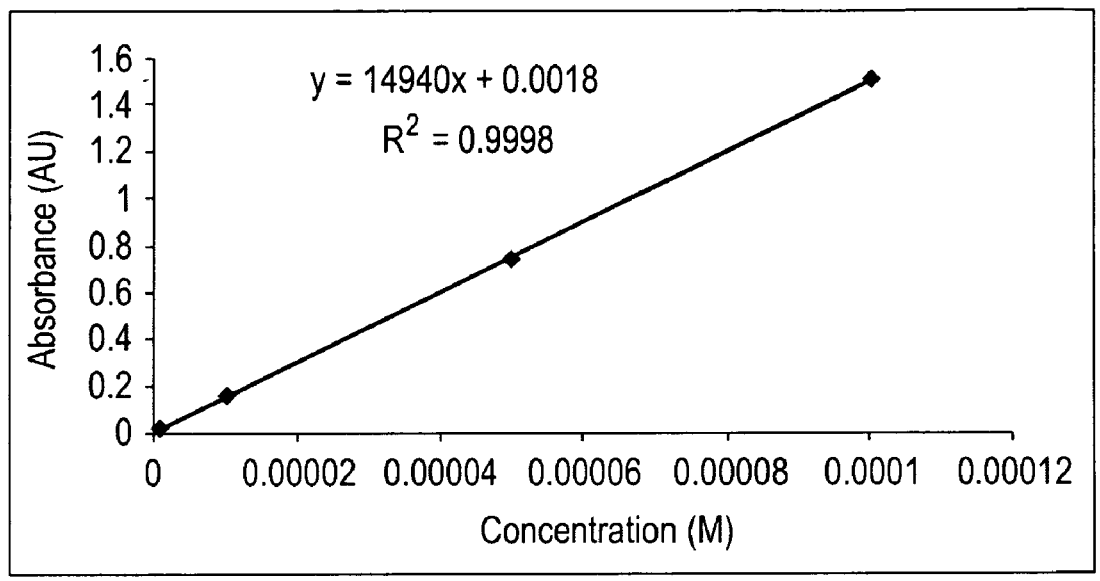
FIG. 5A is a dansyl ethanol calibration curve in water.
Figure 5B:
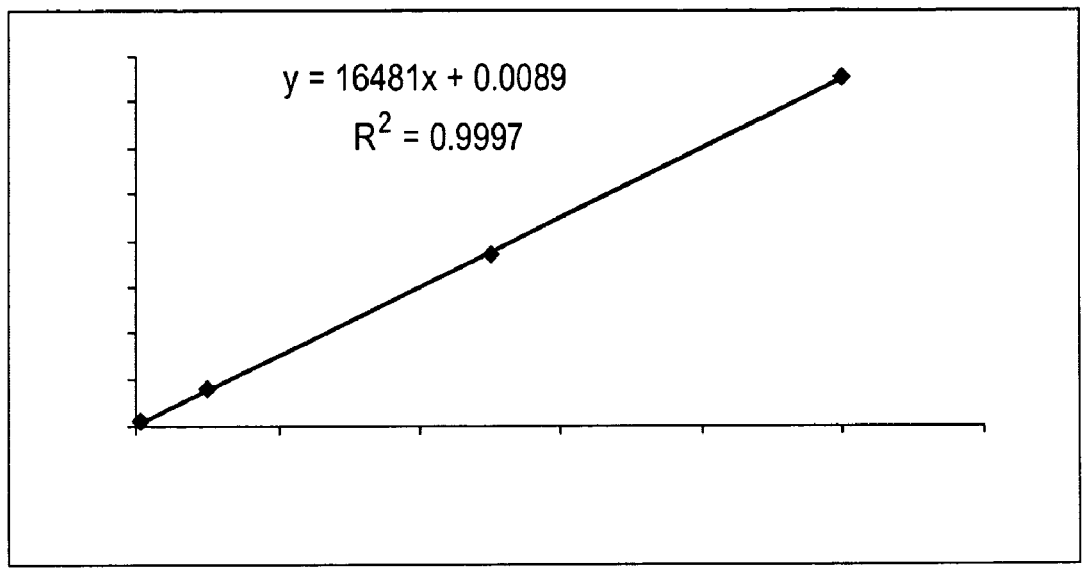
FIG. 5B is a dansyl ethanol calibration curve in octanol.

For the partitioning experiments described below, calibration curves of dansyl ethanol in water and octanol respectively were initially made (see FIGS. 5A-5B). The UV-vis spectra were recorded using an Agilent 8453 spectrophotometer (Agilent, Inc., Santa Clara, Calif.) at λ=335 nm. From the calibration curves, ideal oligomer concentrations were made, which allowed absorbance between 1.0-1.5 instrumentation absorbance units (AU), corresponding to initial oligomer concentrations of ~0.1 mM (in water). After the oligomer was dissolved in water (1 mL), octanol (1 mL) was added and the UV-spectra recorded in both the water and octanol layer. Sodium laurate (1.2 eq to the total guanidine concentration) was added, the vial gently shaken, and the UV spectra recorded in both the water and octanol layer. Following partitioning the water and octanol layers were separated after which the aqueous phase was lyophilized and its contents analyzed with $^1H$-NMR.

Compound 6b (n=11 dansyl functionalized poly(MTC-guanidine)) totally partitioned into the octanol layer following the addition of sodium laurate and UV excitation.

7. Cellular Uptake Assays by Flow Cytometry

Dansyl-tagged oligomers and octaarginine control were brought up in pH 7.2 PBS buffer at 5 μM, 12.5 μM, and 25 μM concentrations. Jurkat cells grown in 10% FBS in RPMI media 1640 (+ glutamine) were used for cellular uptake experiments. Cells were plated on a microtiter plate at 3.0× $10^6$ cells/mL with 200 μL/well. The plate was centrifuged (1300 rpm for 3 min), media removed, and cells resuspended in PBS buffer twice.

Compounds 6(a-c) and the r8 control at varying concentrations were incubated with the cells for 5 minutes at 23° C. The microtiter plates were centrifuged and the cells were isolated, washed with PBS and resuspended in PBS containing propidium iodide (3 μg/mL, 0.01%). The cells were analyzed using a fluorescent flow cytometer (Vantoo, Stanford University) equipped with a UV laser for excitation of the dansyl fluorophore, and cells stained with propidium iodide were excluded from the analysis. The data presented are the mean fluorescent signals for the 20,000 cells analyzed.

Figure 6:
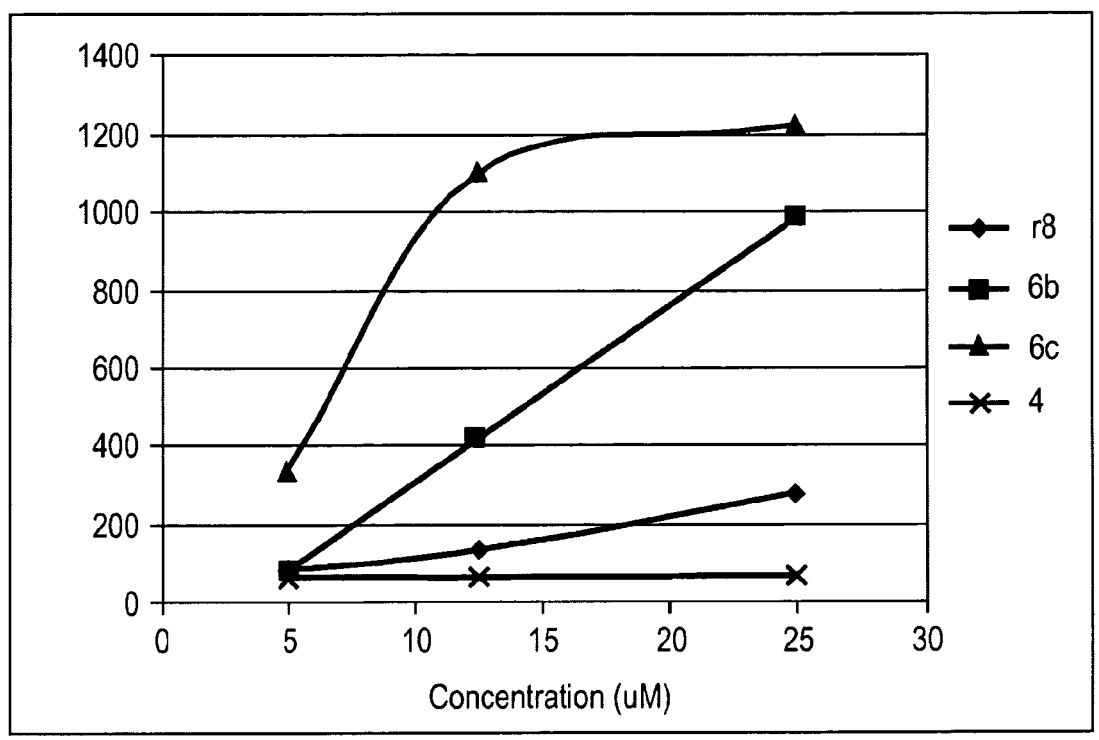
FIG. 6 is a plot of the concentration dependence of cellular uptake into Jurkat Cells with r8 dansyl, Compounds 6a or 6b in Reaction 2, and Compound 4 in Reaction 2.

FIG. 6 shows the concentration dependence of cellular uptake into Jurkat Cells in pH 7.2 PBS, incubated at 5 minutes with r8 dansyl, oligomers Compounds 6a or 6b, or the dansyl alcohol initiator Compound 4 at 23° C.

8. Cellular Uptake Assay at 4° C. or in the Presence of Sodium Azide ($NaN_3$)

Uptake assays at 4° C. were performed as described above except that solutions were precooled at 4° C. and cells were incubated on ice. Uptake assays in the presence of sodium azide were performed as described above with the exception that cells used were preincubated for 30 min with 0.5% sodium azide in 2% FBS/PBS buffer before the addition of fluorescently labeled oligomers and cells were washed with 0.5% sodium azide in PBS buffer.

9. Cellular Uptake Assay in the Presence of High Potassium [K+] Buffer

A high potassium PBS buffer was prepared by mixing 136.9 mmol KCl, 1.5 mmol $KH_2PO_4$, and 8.3 mmol $K_2HPO_4.7H_2O$ and titrated to pH=7.2. Stock solutions of all oligomers were made in the high potassium PBS buffers. Uptake assays were performed as described above with the exception that the cells were washed twice with the high potassium buffer. The cells were then exposed to the oligomer in high [K+] buffer, washed with the same buffer, and finally resuspended in that buffer for analysis.

Figure 7:
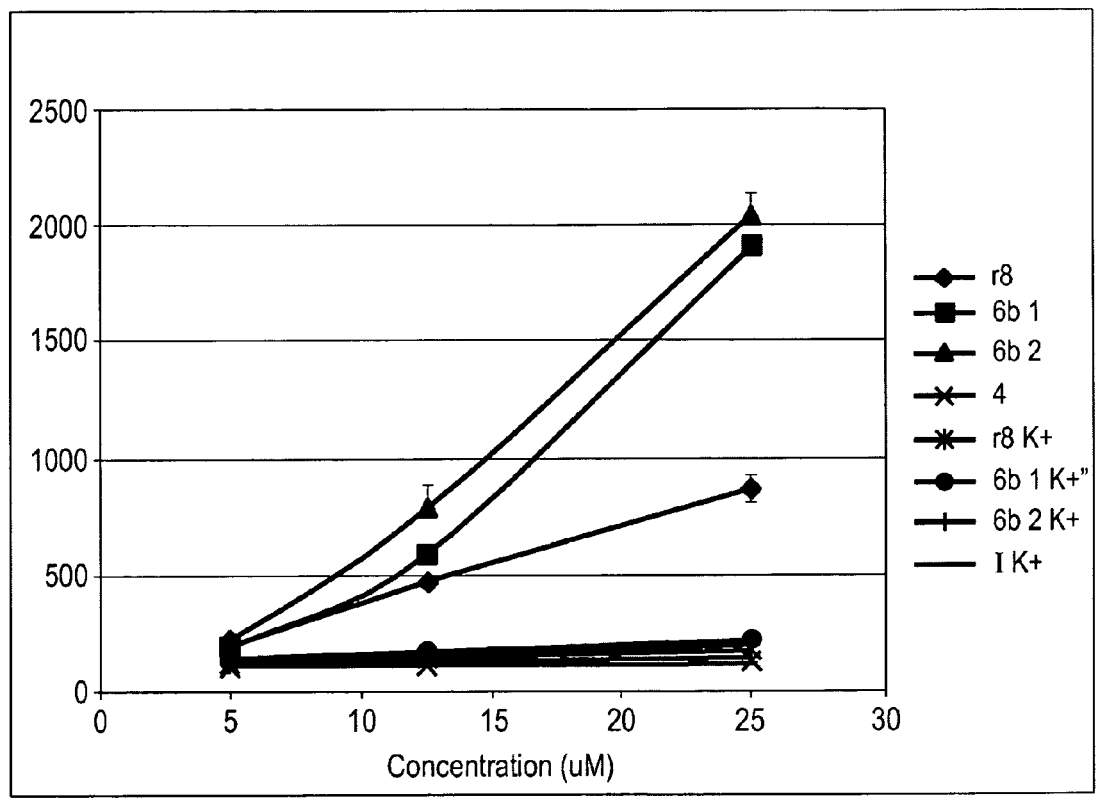
FIG. 7 is a plot of the concentration dependence of cellular uptake into Jurkat Cells in pH 7.2 PBS or K+ PBS, with r8 dansyl, Compounds 6b in Reaction 2, and Compound 4 in Reaction 2.

FIG. 7 is a plot of the concentration dependence of cellular uptake into Jurkat Cells in pH 7.2 PBS or K+ PBS, incubated at 5 minutes with r8 dansyl, oligomers Compounds 6b in two separate batches, 1 or 2, or the dansyl alcohol initiator Compound 4 at 23° C.

Figure 8:
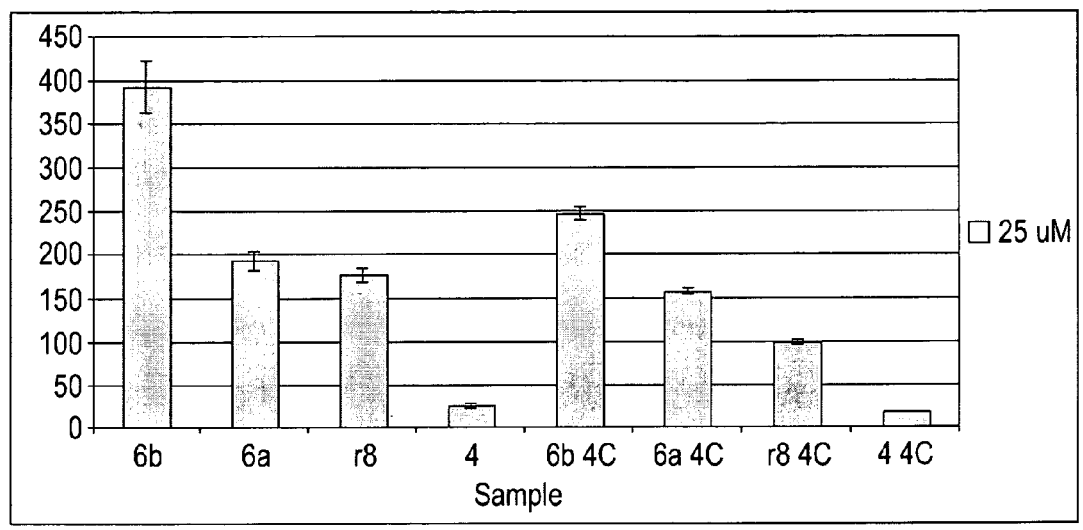
FIG. 8 is a plot of the flow cytometry determined cellular uptake into Jurkat Cells in PBS of Compounds 6a, 6b in Reaction 2, r8 dansyl, and Compound 4 in Reaction 2.

FIG. 8 is a plot of the flow cytometry determined cellular uptake of oligocarbonates Compounds 6a, 6b, r8 dansyl, and dansyl alcohol initiator Compound 4 in PBS. Jurkat cells were incubated with the various transporters for 5 minutes at either 23° C. or 4° C.

Figure 9:
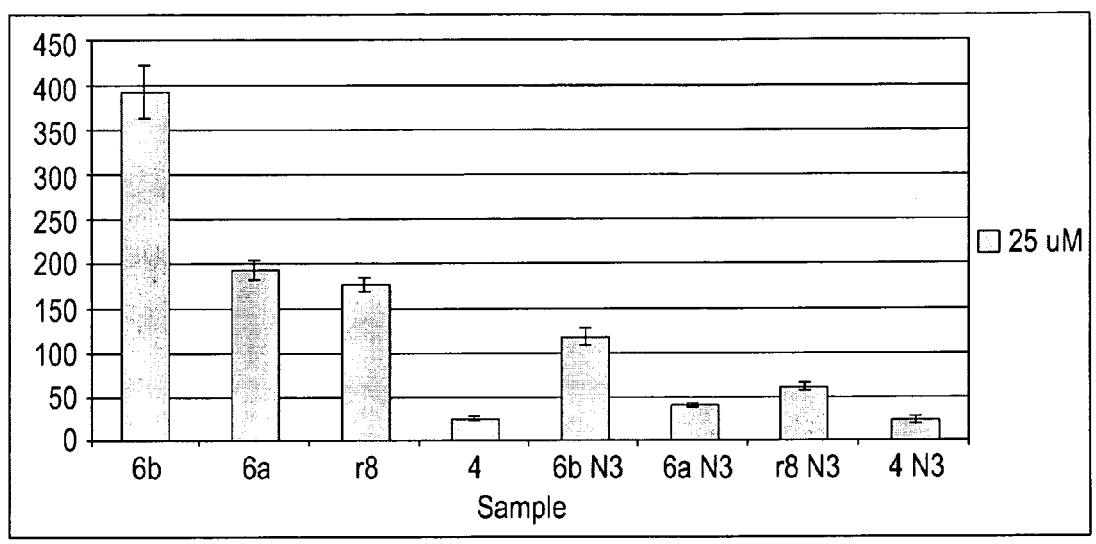
FIG. 9 is a plot of the flow cytometry determined cellular uptake in Jurkat Cells in PBS in the presence/absence of NaN$_3$ for Compounds 6a, 6b in Reaction 2, r8 dansyl, and Compound 4 in Reaction 2.

FIG. 9 is a plot of the flow cytometry determined cellular uptake of oligocarbonates Compounds 6a, 6b, r8 dansyl, and dansyl alcohol initiator Compound 4 in PBS. Jurkat cells were incubated with the various transporters for 5 minutes at 23° C., in the presence and absence of $NaN_3$.

Figure 10:
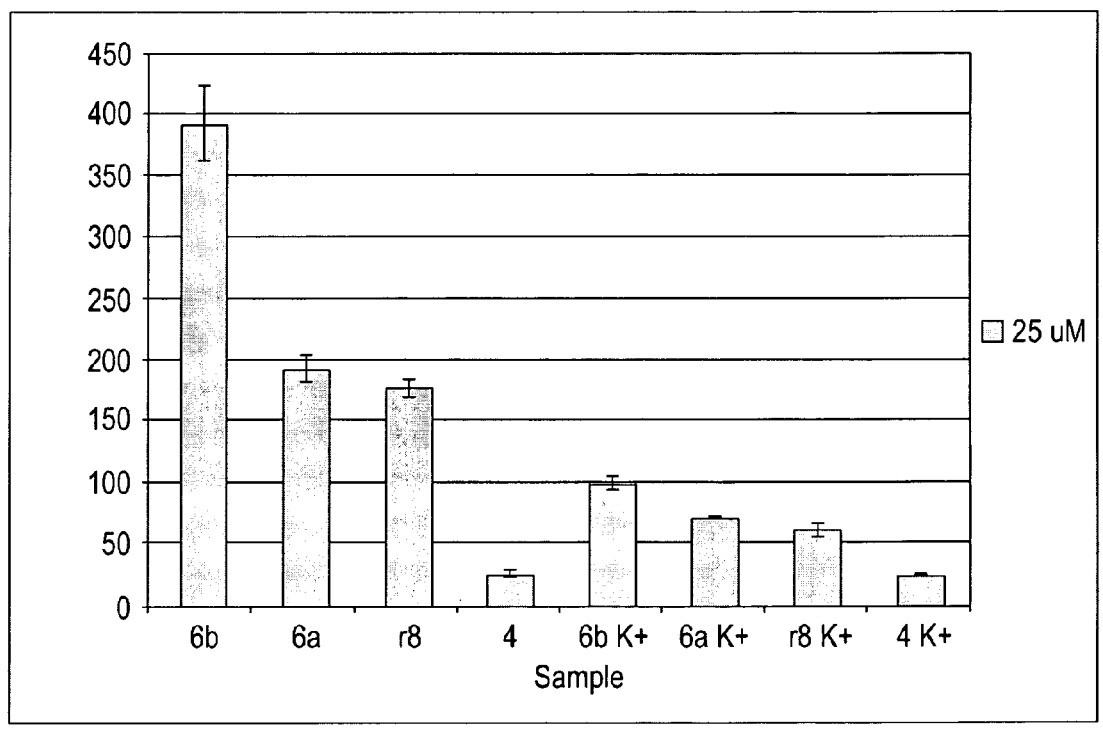
FIG. 10 is a plot of the flow cytometry determined cellular uptake into Jurkat Cells in PBS or [K+] PBS of Compounds 6a, 6b in Reaction 2, r8 dansyl, and Compound 4 in Reaction 2.

FIG. 10 is a plot of the flow cytometry determined cellular uptake of oligocarbonates Compounds 6a, 6b, r8 dansyl, and dansyl alcohol Compound 4 in PBS or [K+] PBS. Jurkat cells were incubated with the various transporters for 5 minutes at 23° C.

10. Results of Cellular Uptake Assays

In contrast to the dansyl initiator 4 alone, which does not enter Jurkat cells, dansyl-oligocarbonate conjugates Compounds 6a-6b exhibited concentration dependent uptake over the range of concentrations studied in a fashion similar to the dansylated r8 positive control. The extended oligomer Compound 6c showed uptake but also competing cell-cell adhesion behavior and was excluded from further analysis. The significant increase in uptake observed for Compound 6b relative to Compound 6a at higher concentrations is consistent with the increase in uptake observed for molecular transporter compounds with increasing guanidine content (up to n=15)[18] and provides further evidence that the GR-oligocarbonates in these embodiments of the present invention are functionally analogous to oligoarginines.

Not unlike the behavior of other polyguanidinylated molecular transporter compounds, the uptake of Compounds 6a-6b decreases with decreasing membrane potential. This effect was established by assaying the uptake of Compound 6 in cells incubated with modified PBS in which all sodium ions were replaced with potassium ions, a protocol known to eliminate the voltage potential across the cell membrane.

Additionally, incubating cells with $NaN_3$, conditions known to interfere with ATP dependent processes, led to a measurable decrease in uptake.

Finally, a decrease (18-37%) in uptake was observed with cells incubated at 4° C., suggesting a mixed mechanistic pathway in which endocytosis could play a role.

11. Fluorescence Microscopy Studies

Cells were washed, incubated with oligomers, and suspended for analysis as described above, with the exception that cells were not stained with propidium iodide before analysis. Analysis was performed on a Zeiss LSM 510 with Ti:Sapphire laser for 2-photon excitation to excite the dansyl fluorophore.

Figure 11:
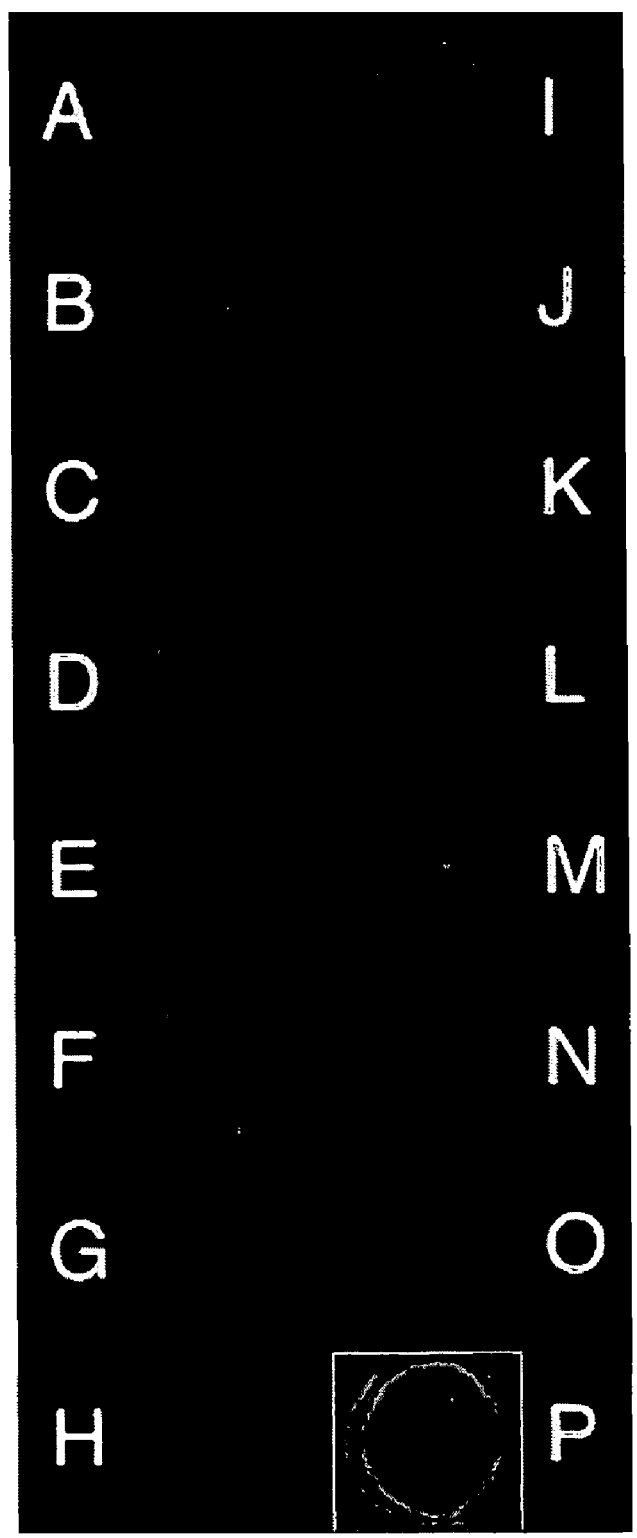
FIG. 11 shows the cellular uptake of Compound 6b in Reaction 2 into Jurkat cells, visualized by fluorescence microscopy using a two-photon excitation. Panels A-O show varying Z-cuts through the cell (from top to bottom), while Panel P shows the bright field image of the same cell.

FIG. 11 shows the cellular uptake of Compound 6b into Jurkat cells, 5 min incubation, 25 μM at 23° C. visualized by fluorescence microscopy using a two-photon excitation. Panels A-O show varying Z-cuts through the cell (from top to bottom) with 0.9 μm resolution and 0.7 μm between cuts. Panel P shows the bright field image of the same cell.

12. Assays Measuring the Hydrolytic Stabilities of the Conjugates:

Each of the conjugates was dissolved in 190 μL HEPES buffered saline (HBS) pH=7.4 (1 mM) in 1.5 mL microfuge tubes and incubated at 37° C. with 10 μL of a solution of 10 mg 1-naphthalenemethanol in 24 mL of methanol, which served as an internal standard. At appropriate time points 20 μL of the solution was removed and analyzed by RP-HPLC. The percent decomposition was calculated from the integrated peak areas of the conjugate, the internal standard, and the various decomposition products.

13. MTT Toxicity Assays:

Jurkat cells grown in 10% FBS in RPMI media 1640 (+ glutamine) were plated at $5$-$10 \times 10^4$ cells/mL on a 96-well microtiter plate in the same media. In a second 96-well plate, compound was serially diluted in triplicate over 20 wells in columns 2-11 and rows 1-3 and 5-7; typical dilutions spanned the concentration range of 400 μM to 20 nM. Columns 1 and 12 contained no cells and no compound, respectively. Rows 4 and 8 contained a serial dilution of colchicine as internal control; colchicine concentrations were generally much lower than compound concentrations in order to obtain an EC50 (half-maximal effective concentration).

Compounds were added to the plate containing cells and the cells were incubated at 37° C. for 24 h, at which point the plate was centrifuged, compound removed, and the cells resuspended in fresh media. The cells were incubated for 24 h., centrifuged, media removed, and 150 μL of 3-(4,5-Dimethylthiazol-2-yl)-2,5-diphenyltetrazolium bromide (MTT) solution (5 mg/mL media) was added to each well. Cells were incubated with MTT for 3 hours at 37° C., 150 μL solubilizing solution (10% triton X-100, 90% 0.1N HCl in isopropanol) was added to each well, and colorimetry data obtained on a plate reader.

Numerical data from plate reader was standardized using values from columns 1 and 12 and curve fitting was performed using Graph Pad Prism software to obtain an EC50 for each compound.

The resulting toxicity and stability data for Compounds 4 and 6a-c are shown in Table 2 below.

TABLE 2

Toxicity and Stability of Oligoguanidines 6a-c

| Compound | EC50 (μM) | Stability ($t_{1/2}$, hours) |
|---|---|---|
| Dansyl-DP8 6a | 17.85 ± 1.07 | 8.3 ± 1.4 |
| Dansyl-DP11 6b | 8.53 ± 0.75 | 8.10 ± 0.14 |
| Dansyl-DP22 6c | 2.32 ± 0.63 | 15.9 ± 0.4 |
| Dansyl initiator 4 | 311 | — |

Various embodiments of the invention have been described. These and other embodiments are within the scope of the following claims.

The invention claimed is:

1. A cyclic carbonate monomer, comprising:

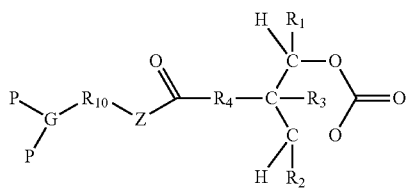

wherein $R^1$, $R^2$, and $R^3$ are independently selected from the group consisting of H, linear or branched, substituted or unsubstituted alkyl;

$R^{10}$ is a connecting group selected from the group consisting of linear or branched, substituted or unsubstituted alkyl, heteroalkyl, cycloalkyl, heterocyclic, aryl and heteroaryl;

$R^4$ is an optional bridging group selected from the group consisting of linear or branched, substituted or unsubstituted alkyl, heteroalkyl, cycloalkyl, heterocyclic, aryl and heteroaryl;

Z is selected from the group consisting of O, NH, NR, and S;

G is a guanidine group; and

P is a protecting group.

2. The monomer of claim 1, wherein P is selected from the group consisting of Boc urethane and benzyl.

3. The monomer of claim 1, wherein the monomer comprises the bridging group $R^4$, and wherein $R^4$ is selected from the group consisting of linear or branched, substituted or unsubstituted alkyl, heteroalkyl, cycloalkyl, heterocyclic, aryl and heteroaryl.

4. The monomer of claim 1, wherein $R^1$ and $R^2$ are H, $R^3$ is $CH_3$, $R^4$ and $R^{10}$ are linear alkyl, and Z is O.

5. An aliphatic carbonate oligomer or cooligomer derived from reacting the monomer of claim 1 with an initiator compound, wherein the initiator compound comprises a functional group selected from the group consisting of amino, hydroxyl, and thiol.

6. The oligomer of claim 5, wherein the functional group on the initiator compound is an hydroxyl group.

7. The oligomer of claim 5, wherein the initiator compound further comprises a biological cargo selected from at least one of a drug, a gene, and a probe.

8. The oligomer of claim 5, wherein the monomer and the initiator compound are reacted in the presence of a catalyst selected from the group consisting of N-heterocyclic carbenes, TBD, thiourea and an amine, phosphazenes, and metal alkoxides.

9. The oligomer of claim 8, wherein the metal alkoxide is selected from the group consisting of LiOR, tin octoate, $Al(OR)_3$, and LZnOR, wherein R is selected from the group consisting of a linear or branched substituted or unsubstituted alkyl or acyl, and L is selected from the group consisting of an alkoxide OR, a β-diketiminate [ArNCHRCHCHRNAr], wherein Ar is a substituted or unsubstituted aryl group, and a tridentate diamino aryloxide.

10. The oligomer of claim 9, wherein the tridentate diamino aryloxide is 2,4,-di-tertbutyl, 6-[2-(dimethylaminoethyl)methylamino] methyl phenolate.

11. The oligomer of claim 8, wherein the catalyst is a combination of a thiourea ArNHC(S)NHR' and at least one of a tertiary amine and a diamine, where Ar is aryl and R' is selected from the group consisting of substituted or unsubstituted aryl and alkyl.

12. The oligomer of claim 11, wherein the thiourea is derived from a compound selected from the group consisting of 3,5-trifluoromethylphenyl, 3,5-dinitrophenyl, and napthyl, and R' is a secondary alkyl selected from the group consisting of cyclohexyl and cyclopentyl.

13. The oligomer of claim 8, wherein the oligomer is derived from reacting the monomer, the initiator, and at least one second monomer.

14. The oligomer of claim 13, wherein the second monomer comprises a biological cargo selected from at least one of a drug, a gene, and a probe.

15. The oligomer of claim 13, wherein the monomer, the initiator, and the at least one second monomer are further reacted with a third monomer.

16. An aliphatic polycarbonate derived from reacting the monomer of claim 1 with an initiator, wherein the initiator is selected from the group consisting of an amine and an alcohol.

17. A method comprising reacting:
(i) a cyclic carbonate monomer comprising

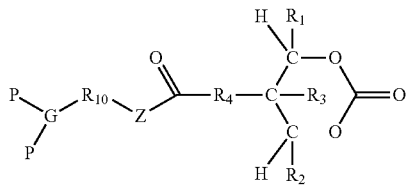

wherein
$R^1$, $R^2$, and $R^3$ are independently selected from the group consisting of H, linear or branched, substituted or unsubstituted alkyl;
$R^{10}$ is a connecting group selected from the group consisting of linear or branched, substituted or unsubstituted alkyl, heteroalkyl, cycloalkyl, heterocyclic, aryl and heteroaryl;
$R^4$ is an optional bridging group selected from the group consisting of linear or branched, substituted or unsubstituted alkyl, heteroalkyl, cycloalkyl, heterocyclic, aryl and heteroaryl;
Z is selected from the group consisting of O, NH, NR, and S;
G is a guanidine group; and
P is a protecting group; and
(ii) a nucleophilic initiator compound comprising at least one of an amino, a hydroxyl, or a thiol functional group, and wherein the initiator compound further comprises a biological cargo selected from at least one of a drug, a gene and a probe;
to open a cyclic ring on a backbone of the cyclic carbonate monomer to form an oligomer with a carbonate backbone and pendant guanidine groups attached to the carbonate backbone, wherein the biological cargo is attached to at least one end of the carbonate backbone.

18. The method of claim 17, wherein the initiator further comprises a protected functional group.

19. The method of claim 18, wherein the functional group comprises a functional group selected from the group consisting of carboxylic acid, amide, ester, protected thiol, amine, and hydroxyl groups.

20. The method of claim 17, further comprising reacting the cyclic carbonate monomer and the initiator with a third monomer, wherein the third monomer comprises a biological cargo selected from at least one of a drug, a gene, and a probe.

21. The method of claim 17, further comprising reacting the oligomer with an acid to provide a oligomeric molecular transporter compound comprising a guanidinium group on the carbonate backbone.

22. The method of claim 17, wherein the cyclic carbonate monomer is derived from reacting a functional cyclic carbonate compound and a functionalized guanidinyl compound.

23. The method of claim 22, wherein the functional cyclic carbonate compound comprises a cyclic carbonate with 5-7 carbon atoms and a carboxylic acid derivative.

24. The method of claim 22, wherein the functionalized guanidinyl compound comprises an alkoxy functional group.

25. The method of claim 17, wherein the oligomer comprises 1 to 50 monomeric units.

* * * * *